US00PP22869P2

(12) United States Plant Patent
Oudolf

(10) Patent No.: US PP22,869 P2
(45) Date of Patent: Jul. 24, 2012

(54) *EUPATORIUM* PLANT NAMED 'SNOWBALL'

(50) Latin Name: *Eupatorium maculatum*
Varietal Denomination: Snowball

(75) Inventor: Petrus Hendricus Oudolf, Hummelo (NL)

(73) Assignee: Future Plants Licentie B.V., Lisserbroek (NA)

( * ) Notice: Subject to any disclaimer, the term of this patent is extended or adjusted under 35 U.S.C. 154(b) by 0 days.

(21) Appl. No.: 12/931,685

(22) Filed: Feb. 7, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para
(74) *Attorney, Agent, or Firm* — C. A. Whealy

(57) ABSTRACT

A new and distinct cultivar of *Eupatorium* plant named 'Snowball', characterized by its upright and relatively compact plant habit; vigorous growth habit; freely basal branching habit; freely flowering habit; creamy white-colored inflorescences; strong peduncles; and good garden performance.

2 Drawing Sheets

Botanical designation: *Eupatorium maculatum.*
Cultivar denomination: 'SNOWBALL'.

BACKGROUND OF THE INVENTION

The present invention relates to a new and distinct cultivar of *Eupatorium* plant, botanically known as *Eupatorium maculatum*, and hereinafter referred to by the name 'Snowball'.

The new *Eupatorium* plant originated during the summer of 2005 from an open-pollination of *Eupatorium maculatum* 'Atropurpureum', not patented, as the female, or seed, parent with an unknown selection of *Eupatorium maculatum*, as the male, or pollen, parent. The new *Eupatorium* plant was discovered and selected by the Inventor as a single flowering plant from within the progeny of the stated open-pollination in a controlled greenhouse environment in Hummelo, The Netherlands during the summer of 2006.

Asexual reproduction of the new *Eupatorium* plant by cuttings in a controlled greenhouse environment in Rijpwetering, The Netherlands since the summer of 2006, has shown that the unique features of this new *Eupatorium* plant are stable and reproduced true to type in successive generations.

SUMMARY OF THE INVENTION

Plants of the new *Eupatorium* have not been observed under all possible environmental conditions and cultural practices. The phenotype may vary somewhat with variations in environment such as temperature and light intensity, without, however, any variance in genotype.

The following traits have been repeatedly observed and are determined to be the unique characteristics of 'Snowball'. These characteristics in combination distinguish 'Snowball' as a new and distinct *Eupatorium* plant:

1. Upright and relatively compact plant habit.
2. Vigorous growth habit.
3. Freely basal branching habit.
4. Freely flowering habit.
5. Creamy white-colored inflorescences.
6. Strong peduncles.
7. Good garden performance.

Plants of the new *Eupatorium* differ primarily from plants of the female parent, 'Atropurpureum', in leaf and flower color as plants of 'Atropurpureum' have very dark green-colored leaves and lilac purple-colored flowers.

Plants of the new *Eupatorium* can be compared to plants of *Eupatorium rugosum* 'Chocolate', not patented. In side-by-side comparisons plants of the new *Eupatorium* differ primarily from plants of 'Chocolate' in the following characteristics:

1. Plants of the new *Eupatorium* are more compact than plants of 'Chocolate'.
2. Plants of the new *Eupatorium* have larger inflorescences than plants of 'Chocolate'.
3. Leaves of plants of the new *Eupatorium* are lighter in color than leaves of plants of 'Chocolate'.

BRIEF DESCRIPTION OF THE PHOTOGRAPHS

The accompanying photographs illustrate the overall appearance of the new *Eupatorium* plant showing the colors as true as it is reasonably possible to obtain in colored reproductions of this type. Colors in the photographs may differ slightly from the color values cited in the detailed botanical description which accurately describe the colors of the new *Eupatorium* plant.

The photograph on the first sheet comprises a side perspective view of a typical flowering plant of 'Snowball' grown in an outdoor nursery.

The photograph at the top of the second sheet is a close-up view of typical inflorescences of 'Snowball'.

The photograph at the bottom of the second sheet is a close-up view of the upper surface of a typical leaf of 'Snowball'.

DETAILED BOTANICAL DESCRIPTION

The aforementioned photographs and following observations and measurements describe plants grown in an outdoor nursery during the autumn in Lisserbroek, The Netherlands and under conditions and practices which approximate those generally used in commercial *Eupatorium* plant production. During the production of the plants, day temperatures ranged from 12° C. to 26° C. and night temperatures ranged from 4° C. to 16° C. Plants were three years old when the photographs and description were taken. In the following description, color references are made to The Royal Horticultural Society Colour Chart, 2007 Edition, except where general terms of ordinary dictionary significance are used.

Botanical classification: *Eupatorium maculatum* 'Snowball'.

Parentage:

*Female parent.*—*Eupatorium maculatum* 'Atropurpureum', not patented.

*Male parent.*—Unknown selection of *Eupatorium maculatum*, not patented.

Propagation:

*Type.*—By cuttings.

*Time to initiate roots, summer.*—About 35 days at 18° C.

*Time to produce a rooted young plant, summer.*—About three months at 18° C.

*Root description.*—Thick, fleshy; reddish brown in color.

*Rooting habit.*—Sparse; density, low.

Plant description:

*Plant and growth habit.*—Herbaceous perennial; upright and relatively compact plant habit; broad inverted triangle; inflorescences held on strong and upright peduncles; vigorous growth habit.

*Plant height.*—About 143 cm.

*Plant diameter or spread.*—About 185 cm.

*Basal branches.*—Quantity: Freely basal branching habit, about 45 per plant. Length (excluding inflorescence): About 103.2 cm. Diameter: About 8 mm. Internode length: About 9.5 cm. Aspect: Mostly upright. Strength: Strong. Texture: Smooth, glabrous. Color: Close to 145B to 145C; blotches, close to 146C.

Foliage description:

*Arrangement.*—Whorled, simple; sessile.

*Length.*—About 14 cm.

*Width.*—About 6.4 cm.

*Shape.*—Ovate.

*Apex.*—Acute to acuminate.

*Base.*—Attenuate.

*Margin.*—Serrate.

*Texture, upper surface.*—Rugose, glabrous.

*Texture, lower surface.*—Pubescent.

*Venation pattern.*—Pinnate.

*Color.*—Developing leaves, upper surface: Close to 137A. Developing leaves, lower surface: Close to 137C. Fully expanded leaves, upper surface: Close to N137A and 147A; venation, close to 152D. Fully expanded leaves, lower surface: Close to 147A to 147B; venation, close to 152D and 153D.

*Petioles.*—Length: About 2.3 cm. Diameter: About 2.7 mm. Color, upper surface: Close to 146B. Color, lower surface: Close to 146C.

Inflorescence description:

*Appearance and flowering habit.*—Discoid inflorescences arranged in terminal and axillary compound corymbs; inflorescences face mostly upright; freely flowering habit; about 13 corymbs develop per branch, each with about 360 to 400 flowers inflorescences.

*Fragrance.*—None detected.

*Time to flower.*—Plants flower continuously from late August to late September in The Netherlands.

*Post-production longevity.*—Inflorescences maintain good substance for about three weeks on the plant; inflorescences persistent.

*Inflorescence bud.*—Height: About 7 mm. Diameter: About 2.5 cm. Shape: Ovoid. Color: Close to 155C; towards the base, close to 193A.

*Corymb diameter.*—About 25.2 cm.

*Corymb height.*—About 29.4 cm.

*Disc diameter.*—About 6 mm.

*Receptacle diameter.*—About 0.5 mm.

*Receptacle height.*—About 0.5 mm.

*Ray florets.*—Ray floret development has not observed.

*Disc florets.*—Shape: Fused in a tube. Apex: Acute. Length: About 1.5 cm. Diameter, apex: About 1 mm. Diameter, base: About 0.5 mm. Number of disc florets per inflorescence: About twelve. Texture: Smooth, glabrous. Color, immature: Close to 155B. Color, mature: Mid-section and towards the apex, close to 155B; base, close to 157C to 157D.

*Phyllaries.*—Quantity per inflorescence: About 15 in about five whorls. Length: About 4 mm. Width: About 1.5 mm. Shape: Narrowly elliptic to narrowly ovate. Apex: Acute. Base: Cuneate. Margin: Entire. Texture, upper and lower surfaces: Smooth, glabrous. Color, upper surface: Close to 155C; towards the base, close to 145A. Color, lower surface: Close to 155C; towards the base, close to 145A; longitudinal stripes, close to 145B to 145C.

*Peduncles.*—Length: About 29.4 cm. Diameter: About 3 mm. Strength: Strong. Aspect: Upright to 35° from vertical. Texture: Smooth, glabrous. Color: Close to 145C to 145D.

*Reproductive organs.*—Androecium: Quantity per floret: About five. Anther shape: Lanceolate. Anther length: About 1 mm. Anther color: Close to 200A. Pollen amount: None observed. Gynoecium: Quantity per floret: One. Pistil length: About 8 mm. Stigma color: Close to NN155D. Style length: About 5 mm. Style color: Close to NN155D. Ovary color: Close to 145A. Seeds and fruits: Seed and fruit development have not been observed.

Disease/pest resistance: Plants of the new *Eupatorium* have not been shown to be resistant to pathogens and pests common to *Eupatorium*.

Garden performance: Plants of the new *Eupatorium* have exhibited good tolerance to rain and wind, and plants have been observed to be hardy to USDA Zone 6 and to tolerate high temperatures of about 35° C.

It is claimed:

1. A new and distinct *Eupatorium* plant named 'Snowball' as illustrated and described.

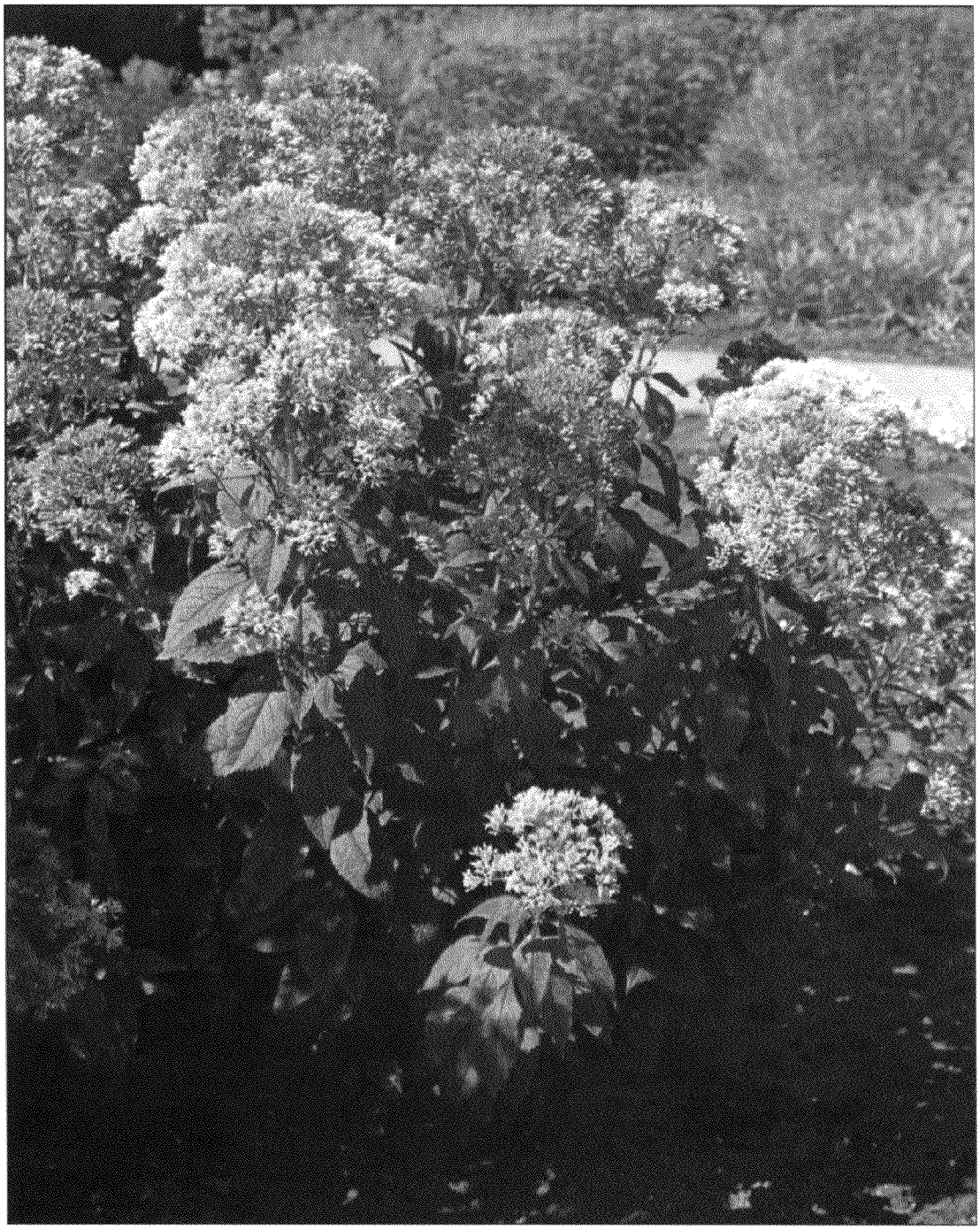

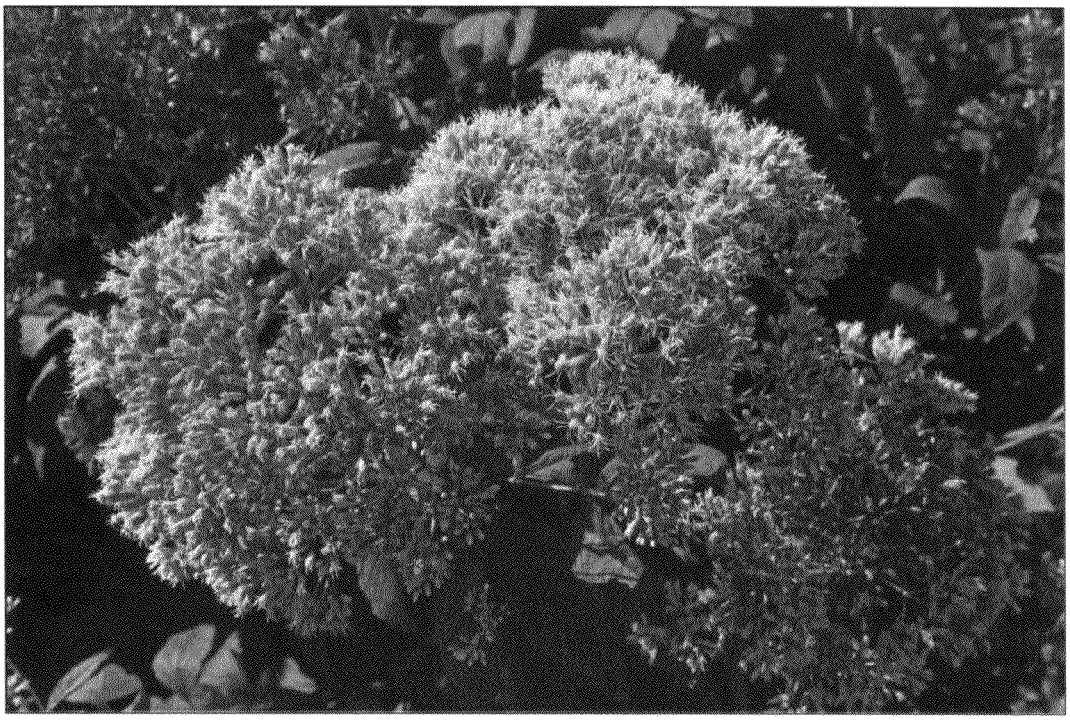
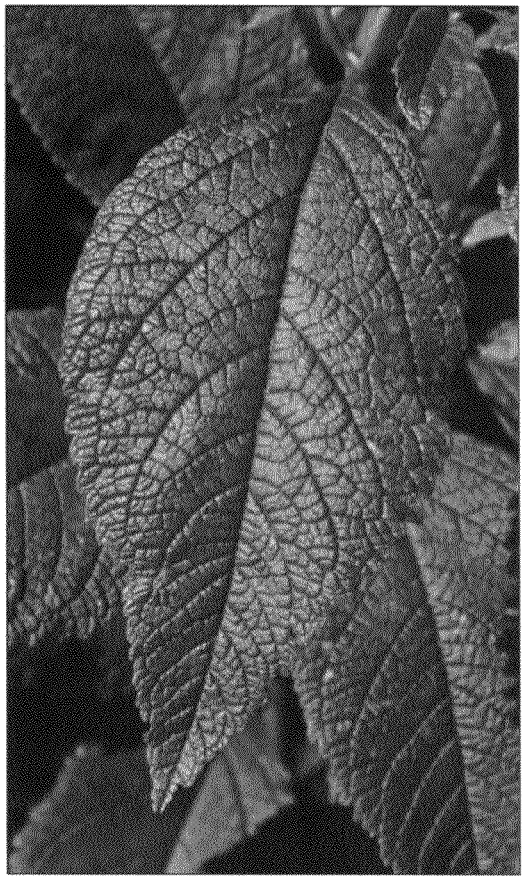

* * * * *